United States Patent
Lehman et al.

(10) Patent No.: US 6,682,925 B1
(45) Date of Patent: Jan. 27, 2004

(54) STREPTOMYCES STRAIN WITH INSECTICIDAL ACTIVITY AND METHOD OF USING AS AN INSECTICIDE

(75) Inventors: Lori Jo Lehman, Vacaville, CA (US); Jimmy Ensio Orjala, Davis, CA (US); Denise Carol Manker, Davis, CA (US); Desmond Rito Jimenez, Woodland, CA (US); Nancy Ann Baum, Davis, CA (US); Pamela Gail Marrone, Davis, CA (US)

(73) Assignee: AgraQuest, Inc., Davis, CA (US)

( * ) Notice: Subject to any disclaimer, the term of this patent is extended or adjusted under 35 U.S.C. 154(b) by 0 days.

(21) Appl. No.: 09/548,882

(22) Filed: Apr. 13, 2000

(51) Int. Cl.$^7$ .............................. C12N 1/20; C12N 1/00
(52) U.S. Cl. .................................... 435/253.5; 435/243
(58) Field of Search ............................ 424/93.4, 93.44; 435/41, 243, 253.5

(56) References Cited

U.S. PATENT DOCUMENTS 5,362,634 A    11/1994  Boeck et al.

FOREIGN PATENT DOCUMENTS

| DE | 3632168 | | 4/1987 |
|---|---|---|---|
| GB | 2324300 | | 10/1998 |
| JP | 01199988 A | * | 9/1989 |
| WO | WO 90/05522 | | 5/1990 |

OTHER PUBLICATIONS

Purcell, J.P. et al., Biochem. Biophys. Res. Commun., 196:1406–1413 (1993).
Sakuda, J.P., Tetrahedron Lett. 27:2475–2478 (1986).
Heisey, R., J. Agric. Food Chem., 36:1283–1286 (1988).
Jizba, J. et al., Folia–Microbiologica 37:461–462 (1992).
Urushibata, I et al., Antibiotics, 46:701–703 (1993).
Box, S.J. et al., Appl. Microbial, 26: 699–704 (1973).
Takahashi, N. et al., Agr. Biol. Chem., 32:1115–1122, (1968).
Nair, M.G. et al., J. Antibiotics 46:1762–1763 (1993).
Carter, G.T. et al., J. Antiobics, 47:1549–1553 (1994).
Nair, M.G. et al., J. Nat. Prod., 52:797–809 (1989).
Zhang, D. et al., J. Antibiotics, 50:617–620 (1997).
Kurokawa, T. et al., J. Antibiotics, 46:1315–1318 (1993).
Zeeck, A. et al., J. Antibiotics 40:1530–1540 (1987).
Zizka, Z. et al., Cytobios, 65:31–38 (1991).
Prikrylova, V. et al., Folia Microbial, 37:386–388 (1992).
Knuessel, I. et al., Comp. Biochem. Phys. B., 120B:639–646 (1998).
Tsuchiya, K.J., J. Antibiotics, 48:626–629 (1995).
Paul, A.K. and Banerjee, A.K., Folia Microbial, 28:386–396 (1983).
Sigmund, J.M. and Hirsch, C.F., J. Antibiotics, 51:829–836 (1998).
Nakayama et al., Agric. Biol. Chem., 51:853–860 (1987).
Achenbach et al., Annals N.Y. Acad. Sci., 544:128–140 (1988).
Mandala et al., J. Biol. Chem., 24:14942–14949 (1998).
Harris et al., J. Antibiotics, 51:837–844 (1998).
Tsuchiya, K., J. Antiobiotics 48:630–634 Jul. (1995).
Fauth, U. et al., J. Antiobiotics 12:1760–1764 Dec. (1986).
English translation of Japanese patent application No. 62–138948 filed on Jun. 4, 1987 entitled "Novel antibiotic IMC29, production method thereof, and acaracides, herbicides and plant virus blight controllers," Publication No. 11–99988 published on Aug. 11, 1989, 21 pages.

* cited by examiner

*Primary Examiner*—Christopher R. Tate
*Assistant Examiner*—Patricia A Patten
(74) *Attorney, Agent, or Firm*—Morrison & Foerster LLP

(57) ABSTRACT

A novel strain of *Streptomyces galbus* that produces metabolites and exhibits pesticidal activity is disclosed. In addition, a supernatant of the novel strain with pesticidal activity is disclosed. An ethyl acetate-soluble, small molecular weight, alkali stable, metabolite produced by the novel strain *Streptomyces galbus* with pesticidal activity against lepidopteran insects is provided. Also included are methods for fermenting the novel strain of *Streptomyces galbus* and increasing the bioactivity of the pesticidal activity. Also included are methods for protecting or treating plants from caterpillars comprising the step of applying to a plant an effective amount of the novel *Streptomyces galbus* strain, the metabolites produced by the strain, or a combination thereof.

19 Claims, No Drawings

STREPTOMYCES STRAIN WITH INSECTICIDAL ACTIVITY AND METHOD OF USING AS AN INSECTICIDE

FIELD OF THE INVENTION

The present invention is in the field of biopesticides. More particularly, this invention relates to a novel strain of Streptomyces with insecticidal activity and methods of use thereof.

BACKGROUND OF THE INVENTION

Natural products are substances produced by microbes, plants, and other organisms. Microbial natural products offer an abundant source of chemical diversity. There is a long history of utilizing these natural products for pharmaceutical purposes. Despite the emphasis on natural products for human therapeutics, there are only a few natural product insecticides for agricultural use. The most successful microbial natural product insecticides are the *Bacillus thuringiensis* toxins, avermectin and the spinosyns. *Bacillus thuringiensis* (*Bt*) bacteria produce cytoplasmic protein crystals (δ-endotoxins) during sporulation which are the most important factor in insect pathogenesis (see, Ellar, D. J. (1997) "The structure and function of *Bacillus thuringiensis* δ-endotoxins and prospects for biopesticide improvement," In: *Microbial Insecticides: Novelty or Necessity*? The British Crop Protection Council Symposium Proceedings No. 68, Coventry, UK). The δ-endotoxins have been used in both spray preparations as well as 'systemic' biopesticides through the introduction of the endotoxin genes into transgenic plants. The growth of the market for the spray preparations of *Bt* is estimated to be around 10% for 1997 through 2000, which will result in a market of $100–$130 million by 2000 (see, Lisansky, S. (1997) "Microbial biopesticides" In: *Microbial Insecticides: Novelty or Necessity*? The British Crop Protection Council Symposium Proceedings No. 68, Coventry, UK.). The main *Bt* transgenic crops are maize and cotton. The transgenic *Bt* maize market in the U.S. has grown from only 1.4% of the planted acreage in 1996 to 19.1% in 1998. The growth in *Bt* cotton has not been as drastic, increasing from 14.6% of the planted acreage in 1996 to 16.8% in 1998. The entire market is currently directed against lepidopteran pests. In 1999, the market for pesticides used against caterpillars in the US exceeded 400 million dollars US.

The avermectins are produced by *Streptomyces avermitilis* during fermentation. Abamectin, one of the naturally occurring macrocyclic lactones, shows activity against mites, pear psylla and diamond back moth. Emamectin, a semi-synthetic analog of abamectin, shows activity against lepidopteran larvae. In invertebrates the avermectins induce the opening of a pre-synaptic chloride ion channel (not GABA-activated), leading to efflux of chloride ions, depolarization of the nerve terminal, and hence, to neurotransmitter release. See, Turner, M. J. and Schaeffer, J. M. (1989) "Mode of action of Ivermectin," In: Ivermectin and Abamectin, W. C. Campbell (Ed.) Springer-Verlag, N.Y. The use of avermectins in insect control had an estimated world market value of $80–$120 million in 1998.

The spinosyns are a new class of fermentation-derived tetracyclic-macrolides produced by the actinomycete *Saccharopolyspora spinosa*. Spinosyns A and D, the principal components of the spinosad insecticide Tracer®, show activity against lepidopteran pests and mosquitoes. See, Sparks, T. C. et al. (1999) "Fermentation-derived insecticide control agents: the spinosyns" In: Biopesticides Use and Delivery, Hall, F. R. et al., eds. Humana Press, Totowa, N.J., pp.155–170. Its mode of action is unique, with a primary site of attack on the nicotine acetylcholine receptor and a secondary attack, possibly on or at GABA receptors. See, Salgado, V. L. (1997) "The modes of action of spinosad and other insect control products" *Down to Earth* 52:35–43.

Streptomyces are a recognized source of insecticidal natural products. In addition to the avermectins and spinosyns, cholesterol oxidase (Purcell, J. P. et al. (1993) *Biochem. Biophys. Res. Commun*. 196:1406–1413), allosamidin (Sakuda, S. (1986) *Tetrahedron Lett*. 27:2475–2478), valinomycin (Heisey, R. (1988) *J. Agric. Food Chem*. 36:1283–1286), pyrrolizine derivatives (Jizba, J. et al. (1992) *Folia-Microbiologica* 37:461–462), respirantin (Urushibata, I. et al. (1993) *J. Antibiotics* 46:701–703), prasinons (Box, S. J. et al. (1973) *Appl. Microbiol*. 26:699–704), piercidin (Takahashi, N. et al. (1968) *Agr. Biol. Chem*. 32:1115–1122) griseulin (Nair, M. G. et al. (1993) *J. Antibiotics* 46:1762–1763), martinomycin (Carter, G. T. et al. (1994) *J. Antibiotics* 47:1549–1553), faeriefungin (Nair, M. G. et al. (1989) *J. Nat. Prod*. 52:797–809), indanomycin (Zhang, D. et al. (1997) *J. Antibiotics* 50:617–620), cyclophostin (Kurokawa, T. et al. (1993) *J. Antibiotics* 46:1315–1318), manumycin (Zeeck, A. et al. (1987) *J. Antibiotics* 40:1530–1540), ichthyomycin (Zizka, Z. et al. (1991) *Cytobios* 65:31–38), virginiamycin (Prikrylova, V. et al. (1992) *Folia Microbiol*. 37:386–388), suidatestrin (Knuessel, I., et al. (1998) *Comp. Biochem. Phys. B*. 120B:639–646), gualamycin (Tsuchiya, K. J. (1995) *J. Antibiotics* 48:626–629), and other insecticidal natural products have been reported from Streptomyces strains.

*Streptomyces galbus* is recognized for its production of the potent anti-botrytis macrolides, galbonolide A and galbonolide B. (Paul A. K. and Banerjee, A. K. (1983) *Folia Microbiol*. 28:386–396; Sigmund, J. M. and Hirsch, C. F. (1998) *J. Antibiotics* 51:829–836; Achenbach, H., DE Patent No. 86-3632168; and Zaehner, H., DE Patent No. 3632168). Nakayama et al. (1987) *Agric. Biol. Chem*. 51:853–860, reported the discovery of rustmicin, a potent inhibitor of wheat stem rust, *Puccinia gramnis*. Later, galbonolide A was shown to be the same molecule as rustmicin. Achenbach et al. (1988) *Annals N.Y. Acad. Sci*. 544:128–140, reported galbonolide A to be much more active than galbonolide B against a number of endomycetous yeasts and a large number of Deuteromycetes such as *Candida albicans* and *Botrytis cinerea*. No evidence for ionophoric activity, membrane destabilization, interference with DNA or RNA biosynthesis, or inhibition of chitin biosynthesis could be attributed to these macrolides. Recently Mandala et al. (1998) *J. Biol. Chem*. 24:14942–14949) and Harris et al. (1998) *J. Antibiotics* 51:837–844; and Harris, G., et al. Patent No. GB 2324300) demonstrated that rustmicin inhibits inositol phosphoceramide synthetase, the first fungal-specific-enzyme in sphingolipid biosynthesis. We now document the potent insecticidal properties of a novel strain of *S. galbus*, with activity against a number of agriculturally relevant Lepidoptera.

DESCRIPTION OF THE INVENTION

The present invention provides a novel compound, *Streptomyces galbus*, NRRL Accession No. 30232, and mutants thereof which retain the same activity, for use as an insecticide against Lepidoptera. The invention encompasses the use of supernatants and metabolites from the strain for use as an insecticide. The invention also includes methods of treating plants or fruit to control Lepidoptera infestations using the claimed strain, either alone, or in combination with other chemical or biological pesticides. Further provided are methods to ferment the claimed strain to increase its bioactivity as an insecticide.

MODES FOR CARRYING OUT THE INVENTION

Deposit of Microorganisms

A strain of *Streptomyces galbus* was deposited on Dec. 10, 1999 according to the Budapest Treaty in the Agricultural Research Service Patent Culture Collection (NRRL), Northern Regional Research Center, 1815 University Street, Peoria, Illinois, 61604, USA. The Accession number is NRRL 30232.

The strain has been deposited under conditions that assure that access to the culture will be available during the pendency of this application. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

Definitions

As used herein, certain terms may have the following defined meanings.

The singular form "a," "an" and "the" include plural references unless the context clearly dictates otherwise. For example, the term "a cell" includes a plurality of cells, including mixtures thereof.

The term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and agriculturally acceptable carriers. "Consisting of" shall mean excluding more than trace elements of other ingredients and substantial method steps for applying the compositions of this invention. Embodiments defined by each of these transition terms are within the scope of this invention.

As used herein, "biological control" is defined as control of a pathogen or insect by the use of a second organism. Known mechanisms of biological control include enteric bacteria that control root rot by out-competing fungi for space on the surface of roots, or the application of *Bacillus thuringiensis* to control insect pests. Bacterial toxins, such as antibiotics, have been used to control pathogens and insects. The toxin can be isolated and applied directly to the plant or the bacterial species may be administered so it produces the toxin in situ.

The term "fungus" or "fungi" includes a wide variety of nucleated spore-bearing organisms that are devoid of chlorophyll. Examples of fungi include yeasts, molds, mildews, rusts, and mushrooms.

The term "bacteria" includes any prokaryotic organism that does not have a distinct nucleus.

"Fungicidal" or "anti-fungal" means the ability of a substance to increase mortality or inhibit the growth rate of fungi.

"Antibiotic" includes any substance that is able to kill or inhibit the growth of another living organism, including, but not limited to other microorganisms. Antibiotics may be produced by a microorganism or by a synthetic process or semi-synthetic process.

The term "mutant" refers to a variant of the parental strain as well as methods for obtaining a mutant or variant in which the pesticidal activity is greater than that expressed by the parental strain. The "parent strain" is defined herein as the original Streptomyces strain before mutagenesis. To obtain such mutants the parental strain may be treated with a chemical such as N-methyl-N'-nitro-N-nitrosoguanidine, ethylmethanesulfone, or by irradiation using gamma, x-ray, or UV-irradiation, or by other means well known to those practiced in the art.

A "variant" is a strain having all the identifying characteristics of NRRL Accession No. 30232 and can be identified as having a genome that hybridizes under conditions of high stringency to the genome of NRRL Accession No. B-30232. "Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. Hybridization reactions can be performed under conditions of different "stringency." In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

A variant of NRRL Accession No. 30232 may also be defined as a strain having a genomic sequence that is greater than 85%, more preferably greater than 90% or more preferably greater than 95% sequence identity to the genome of NRRL Accession No.

B-30232. A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example, those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/cgi-bin/BLAST.

The term "culturing" refers to the propagation of organisms on or in media of various kinds.

"Whole broth culture" refers to a liquid culture containing both cells and media.

"Supernatant" refers to the liquid broth remaining when cells grown in broth are removed by centrifugation, filtration, sedimentation, or other means well known in the art.

An "effective amount" is an amount sufficient to effect beneficial or desired results. An effective amount can be administered in one or more administrations. In terms of treatment and protection, an "effective amount" is that amount sufficient to reduce, retard, or eliminate an insect's ability to feed, grow, and reproduce in the pre-adult or adult stage of development.

As used herein, the term "insect" includes all organisms in the class Insecta.

As used herein the term "Lepidoptera" refers to the insect order characterized by a larval stage taking the form of a caterpillar or worm and an adult stage taking the form of a moth or a butterfly.

A "pre-adult" insect refers to any form of an organism prior to the adult stage, including, for example, eggs, larvae, and nymphs.

"Insecticidal" refers to the ability of a substance to increase mortality or inhibit the growth rate of insects.

"Pesticidal" refers to the ability of a substance to increase mortality or inhibit the growth rate of insects, nematodes and mites.

"Positive control" means a compound known to have pesticidal activity. "Positive controls" include, but are not limited to commercially available chemical pesticides.

The term "negative control" means a compound known not to have pesticidal activity. Examples of negative controls are water, media blanks, or low concentrations of solvent such as acetone, ethanol, or ethyl acetate.

Media blanks are composed of sterilized fermentation broth in the absence of a fermenting microorganism.

The term "solvent" includes any liquid that holds another substance in solution.

"Solvent extractable" refers to any compound that dissolves in a solvent and which then may be isolated from the solvent. Examples of solvents include, but are not limited to, organic solvents like ethyl acetate (EtOAc), acetone, ethanol (EtOH), acetonitriles, methanol (MeOH), butanol (BuOH), or dimethylsulfoxide (DMSO).

The term "metabolite" refers to any compound, substance or by product of the fermentation of a microorganism that has biological activity.

A "composition" is intended to mean a combination of active agent and another compound, carrier or composition, inert (for example, a detectable agent or label or liquid carrier) or active, such as an adjuvant.

This invention provides a biologically pure culture of a strain having all the identifying characteristics of *Streptomyces galbus*, NRRL Accession No. 30232, and its variants and mutants, as described above, that have insecticidal activity. In one embodiment, the invention is the strain designated NRRL Accession No. 30232.

This invention provides a process for isolating a metabolite from the biologically pure cultures of strains described herein as well as the metabolites isolated thereby. The metabolite is characterized as being solvent extractable and having a molecular weight of less than 10,000 Daltons.

Further provided is a process for purifying biologically active supernatants from the biologically pure cultures identified herein and the supernatants isolated thereby. The isolated supernatants have insecticidal activity similar to that of a *Streptomyces galbus*, NRRL Accession No. 30232, or mutants and variants thereof.

Also provided by this invention are compositions comprising at least one of the biologically pure cultures, supernatants or the isolated metabolite described above and a carrier. In another aspect, the composition further contains at least one chemical or biological pesticide. The compositions are formulated as any one or more of a wettable powder, a granule, an aqueous suspension, and emulsifiable concentrate and a microencapsulated formulation.

In order to achieve good dispersion and adhesion of compositions within the present invention, it may be advantageous to formulate the whole broth culture, supernatant, fraction and/or metabolite/antibiotic with components that aid dispersion and adhesion. Accordingly, suitable formulations will be known to those skilled in the art (wettable powders, granules and the like, or can be microencapsulated in a suitable medium and the like, liquids such as aqueous flowables and aqueous suspensions, and emulsifiable concentrates). Other suitable formulations will be known to those skilled in the art.

Any of the above noted strains, metabolites, fractions, supernatants and compositions containing these active ingredients, may be used to provide a method of treating or protecting plants, roots or fruit from insect infections. Insects include, but are not limited to an insect selected from the group consisting of Lepidoptera, Coleoptera and Diptera. In one aspect, the insect is Lepidoptera, e.g., *Spodoptera exigua, Anticarsia gemmatalis*, Plutella spp., *Helicoverpa zea, Heliothis virescens*, and *Trichoplusia ni*.

Also provided by this invention is a method for producing a supernatant active as an insecticide by culturing the strains of this invention and isolating the supernatant. The supernatant produced by this method is also claimed herein.

The metabolite is isolated by reverse phase, solid phase extraction using a step gradient of methanol and water. The metabolite can be identified by its molecular weight (less than 10,000 Daltons).

All patents and publications cited herein are incorporated by reference. The following examples are provided to illustrate the invention. These examples are not to be construed as limiting.

EXAMPLES

The following examples are intended to illustrate, but not limit the invention.

Example 1

Characterization of *Streptomyces galbus*, strain NRRL Accession No. 30232

NRRL Accession No. 30232 was identified based on 16S rRNA sequencing. The protocol used to generate the 16S rRNA gene data sequence (Acculab Customer Handbook v. 1.0) is described as follows.

The 16S rRNA gene is PCR amplified from genomic DNA isolated from bacterial colonies. Primers used for the amplification correspond to *E. coli* positions 005 and 531. Amplification products are purified from excess primers and dNTPs using Microcon 100 (Amicon) molecular weight cut-off membranes and checked for quality and quantity by running a portion of the products on an agarose gel.

Cycle sequencing of the 16S rRNA amplification products is carried out using AmpliTaq FS DNA polymerase and dRhodamine dye terminators. Excess dye-labeled terminators were removed from the sequencing reactions using a Sephadex G-50 spin column. The products are collected by centrifugation, dried under vacuum and frozen at −20° C. until ready to load. Samples are re-suspended in a solution of formamide/blue dextran/EDTA and denatured prior to loading. The samples are electrophoresed on an ABI Prism 377 DNA Sequencer. Data are analyzed using PE/Applied Biosystem's DNA editing and assembly software. Once obtained, sequences are compared against PE/Applied Biosystem's MicroSeq™ database using MicroSeq™ sequence analysis software. Sequences are also compared to the GenBank and Ribosomal Database Proiect (RDP).

The result of the 16S rRNA sequencing identified NRRL No. 30232 as *Streptomyces galbus* with a %ID score of 99% (GenBank) and a similarity rank of 0.98 (RDP). These scores indicate a match at the species level.

Example 2

Activity of *Streptomyces galbus*, NRRL Accession No. 30232 against plant pathogens chemical controls scored index ratings of one (1) in all of the independent replicated tests; and media blanks had ratings of five (5).

TABLE 1

Fungicidal activity of NRRL Accession No. 30232

| Replicate | Media | Conc. | ABRA | BOTC | MONF | PCAP | PSTO | COLC |
| --- | --- | --- | --- | --- | --- | --- | --- | --- |
| Rep 1 | 6 | 1× Super | 4 | 5 | 5 | 3 | 5 | 4 |
| Rep 1 | 31 | 1× Super | 5 | 4 | 3 | 3 | 5 | 4 |
| Rep 1 | 38 | 1× Super | 5 | 5 | 4 | 3 | 5 | 4 |
| Rep 2 | 31 | 1× Super | 5 | 4 | 4 | 4 | 4 | 4 |
| Rep 2 | 38 | 1× Super | 5 | 5 | 5 | 5 | 5 | 4 |
| Rep 2 | 38 | 1× Super | 5 | 5 | 4 | 3 | 5 | 3 |
| Rep 3 | 6 | 1× Super | 5 | 4 | 5 | 0 | 5 | 5 |
| Rep 3 | 31 | 1× Super | 5 | 5 | 2 | 0 | 5 | 3 |

The novel *Streptomyces galbus* strain was grown for testing against plant pathogens in the following manner. The isolated microbe was initially fermented in three distinct actinomycete cultivation media. Media 38 was composed of 2 g/L tomato paste, 2 g/L oat flour, and 1.0 g/L sea salts. Media 31 was composed of 45 g/L oat flour, 2 g/L yeast extract, 6 g/L $KH_2PO_4$, and 4.8 g/L $Na_2HPO_4$, pH 7. Media 6 was composed of 20 g/L soluble starch, 10 g/L dextrose, 5 g/L yeast extract, 5 g/L N-Z amineA, and 1 g/L $CaCO_3$.

The microbe was picked from tomato-oat flour agar (2 g/L tomato paste, 2 g/L oat flour, and 20 g/L agar) and introduced to 50 ml conical tubes containing 12 ml of sterile fermentation media capped with a foam plug. The inoculated tubes were incubated at 27±3° C., in an orbital shaker for six days. The tubes of small-scale fermentation product were spun at 4,200 rpm (3,500 g-forces) for 15 minutes using a swing bucket rotor (JS4.2) in a Beckman JB-6 refrigerated centrifuge. The supernatants were collected aseptically and transferred into sterile 96 deep well plates or five ml tubes in racks amenable to automation. Each supernatant was transferred aseptically, in triplicate, into sterile 96-well microtiter plates. Chemical controls were added as positive checks along with media blanks and water controls. Layers of molten agar were then overlaid in stepwise fashion.

The 25 micro liter ($\mu$l) aliquots of supernatant were overlaid with 75 $\mu$l of molten 2.5% agar followed by 100 $\mu$l aliquots of 0.75% Potato Dextrose Agar (Potato Dextrose Broth 23 g/L, agar 7.5 g/L). Finally, 25 $\mu$l of a pathogen spore suspension was overlaid on top of the PDA and the plates were incubated at 24±2° C. for four days. Pathogen growth was rated using a scaled index in which five indicated growth equal to the water control, and a rating of one indicated the complete absence of growth. Index values two (2) through four (4) represent intermediate levels of sporulation and growth whereas zero (0) indicates a failed or unnecessary test.

The following pathogen/chemical pairs were tested: *Alternaria brassisicola* (ABRA Benomyl), *Botrytris cinerea* (BOTC/Benomyl), *Monilinuafructicola* (MONF/Benomyl), *Phytophthora capsici* (PCAP/Metalaxyl), *Pseudomonas syringae* (PSTO/Gentamycin), and *Colletotrichum coccoides* (COLC/Chlorothalonil). Table 1 shows the results of three distinct replicated tests. The tests comprised three separate fermentation dates and are documented below. The Although there was some slight inhibition of the pathogens tested in some of the wells, particularly PCAP Rep 1, the results did not conclusively confirm in Rep 2. Overall, the data show that the whole broth supernatant of a six-day-old culture of the novel strain NRRL Accession No. 30232 was not generally active against plant pathogen spores in an agar diffusion type assay.

Example 3

Activity of *Streptomyces galbus*, NRRL Accession No. 30232 against insects

To assess insecticidal activity, six replicates of each microbial extract were overlaid on top of a wheat germ/casein-based artificial diet in 96-well plates (29 g/L agar, 13.8 g/L Celufil, 38.5 g/L sucrose, 32.2 g/L casein, 27.5 g/L wheat germ, 9.2 g/L Wesson salt mix, 9.0 g/L vitamin premix, 33 mg/L streptomycin, 33 mg/L chlorotetracycline hydrochloride, 1.2 ml/L proprionic acid, 0.12 ml/L phosphoric acid, 10 ml/L 100 proof ethanol, 1 g/L methyl paraben, 0.3 g/L sodium benzoate, 1.0 g/L sorbic acid). Temporally synchronized beet armyworm eggs were sanitized and suspended in a dilute agar solution. Inverted Millipore® 96-well filtration plates were used as a template to inoculate rectangles of Whatman® #2 filter paper with five to ten, seven-day-old eggs in 25 $\mu$l. The filter paper was allowed to dry, inverted and matched to the well orifices of the diet/extract plate. The filter papers were covered with a ventilated plate lid and taped in place. The plates were incubated in a Percival growth chamber at 28±2° C., under a 16:8 photoperiod, at 30–40% relative humidity. The eggs hatched and the neonates dropped to the extract-treated diet. After four days the plates were removed from the Percival, the cellophane tape removed, and the plates were dropped onto a tabletop to remove worms from the filter paper. The lid/filters were replaced with a perforated piece of transparent Mylar and sealed in place with a hot iron. The test was returned to the Percival for one additional day. Larval growth was rated visually using an index similar to the plant pathology screen where a rating of one indicated 100% mortality and a rating of four indicated growth equal to untreated controls. A rating of two indicates less than 100% but greater than 50% mortality or severely stunted growth. A rating of three indicates less than 50%, but greater than 25% mortality or stunting. A chemical control plate was run for each replicated experimental date. Eight serial dilutions of Javelin® (*Bacillus thuringiensis* kurstaki strain), from 1000 to 7 PPM yielded dose response data. Western spotted cucumber beetles (CRW: *Diabrotica undecimpunctata*) were tested in a similar assay using bifenthrin as a chemical control. Green peach aphids (GPA: *Myzus persicae*) or Pea aphids (PA: *Acyrthosiphon pisum*) were tested in 96-well plate assays. Supernatants were absorbed onto filter paper disks in the bottom of 96-well plates. Aphids were placed in the wells and Millipore® 96-well filter plates fitted with parafilm membranes were used to cover the base plate. Filter plate wells were loaded with 40 $\mu$l of supernatant and 40 $\mu$l of artificial liquid diet (300 g/L sucrose, 10 g/L casein hydrosylate, 1 g/L Wesson salt mix, 1 g/L vitamin premix, 33 mg/L streptomycin, 33 mg/L chlorotetracycline hydrochloride, 1 g/L methyl paraben, 0.3 g/L sodium benzoate, 1.0 g/L sorbic acid, pH 6.8). Chemical control plates were treated with serial dilutions of imidocloprid in which base plate-treated filter paper detected contact-activity and membrane-treated wells detected ingested-active. Aphid mortality was read after 24 to 48 hours. The number of living aphids feeding on water/diet control membranes and walking/resting in the wells with water treated filter paper were tabulated. Upper and lower limits and their standard deviation were calculated allowing index range calculations. Two-spotted spider mites (SM: *Tetranynchus orticae*) were evaluated using 96-well plates with filter papers. Supernatants (40 $\mu$l) were pipetted on to filter papers followed by 20 $\mu$l aliquots of artificial liquid diet and the plates were partially dried under forced air. Mortality was evaluated after 24–48 hours. Serial dilutions of avermectin were used as chemical controls. Round worms (CE: *Caenorhabditis elegans*), entomopathogenic nematodes (HB: *Heterorhabditis bacteriophora*) and root knot nematodes (MJ: *Meloidogyne javonica*) were evaluated as liquid suspensions of J2s in 96-well plates. Avermectin® was used as a chemical control.

The data in Table 2 show the specificity of NRRL Accession No. 30232 against beet armyworm. ATCC Accession No. 49460 is the American Type Culture Collection wild-type isolate of *Saccharopolyspora spinosa*—an organism that produces spinosyns. See, Sparks et al. (1999) "Fermentation-derived insecticide control agents: the spinosyns" In: Biopesticides, Use and Delivery, Hall F. R. et al., eds., Humana Press, Totowa, N.J., pp. 155–170. As shown in Table 2, below, both ATCC Accession No. 49460 and NRRL Accession No. 30232 were active against beet armyworm in media 31.

TABLE 2

Insecticidal activity of NRRL 30232 and ATCC 49460

| Replicate | Sample | Media | Conc. | CE | CRW | BAW | GPA | SM |
|---|---|---|---|---|---|---|---|---|
| Rep 1 | 30232 | 31 | 1× Super | 4 | 4 | 1 | 4 | 4 |
| Rep 1 | 30232 | 38 | 1× Super | 4 | 3 | 2 | 4 | 4 |
| Rep 1 | 49460 | 31 | 1× Super | 0 | 0 | 1 | 0 | 0 |
| Rep 2 | 30232 | 31 | 1× Super | 0 | 0 | 1 | 0 | 0 |
| Rep 2 | 30232 | 38 | 1× Super | 0 | 0 | 1 | 0 | 0 |
| Rep 2 | 49460 | 31 | 1× Super | 0 | 0 | 2 | 0 | 0 |
| Rep 3 | 30232 | 31 | 1× Super | 0 | 0 | 4 | 0 | 0 |
| Rep 3 | 30232 | 38 | 1× Super | 0 | 0 | 1 | 0 | 0 |
| Rep 3 | 49460 | 31 | 1× Super | 0 | 0 | 2 | 0 | 0 |
| Rep 4 | 30232 | 31 | 1× Super | 0 | 0 | 1 | 0 | 0 |
| Rep 4 | 30232 | 38 | 1× Super | 0 | 0 | 1 | 0 | 0 |

Example 4

Chemical Characteristics of the Insecticidal Metabolites Produced by NRRL Accession No. 30232

To determine the stability of the active principle, 1 ml aliquots of the whole broth were adjusted to pH 1 with 2N hydrochloric acid (HCl). After one hour the pH was readjusted to 7 with 2N sodium hydroxide (NaOH). Similarly, 1 ml aliquots of the whole broth were adjusted to pH 10 with 2N NaOH. After 1 hr the pH was readjusted to 7 with 2N HCl. The activity was lost during the acid treatment, but remained under basic conditions.

To determine the extractability of the active principle, 20 ml aliquots of the whole broth were partitioned with ethyl acetate, 3 times with 20 ml each, (total extract 60 ml) and subsequently with water saturated n-butanol (BuOH), 3 times with 20 ml each, (total extract 60 ml). All of the fractions, including the remaining aqueous phase were dried and then re-suspended. Dried EtOAc extracts were suspended in acetone: water, the BuOH fractions were suspended in EtOH: water and the remaining aqueous phase was re-suspended in water to bring it back to the equivalent of 1× broth. Combined fractions consisted of equal volumes from each phase. The EtOAc fraction was found to contain the majority of the active metabolite, with a small portion trailing into the BuOH fraction, when assayed at 1×. At more dilute concentrations (¼×) the activity was only observed in the EtOAc fraction.

A 10 ml whole broth equivalent of the EtOAc fraction in 200 $\mu$l of acetone was further purified by reversed phase (RP) solid phase extraction (Bakerbond spe, octadecyl) using a step gradient of 25% MeOH: water, 50% MeOH: water, 75% MeOH: water, and 100% MeOH. The active metabolite eluted with 100% MeOH.

The data in Table 3, below, shows the results from four extractions-partitions, two reverse-phase chromatographies, and two pH tests.

TABLE 3

Bioactivity of NRRL Accession No. 30232; extracts, partitions, RP chromatography, and altered pH

| Replicate | Sample | Conc. | BAW |
|---|---|---|---|
| Rep 1 | Whole Broth | 1x | 1.0 |
| Rep 1 | EtOAc | 1x | 1.0 |
| Rep 1 | BuOH | 1x | 1.0 |

TABLE 3-continued Bioactivity of NRRL Accession No. 30232; extracts, partitions, RP chromatography, and altered pH

| Replicate | Sample | Conc. | BAW |
|---|---|---|---|
| Rep 1 | Aqueous | 1x | 4.0 |
| Rep 1 | Combined | 1x | 1.0 |
| Rep 1 | Whole Broth | .25x | 2.0 |
| Rep 1 | EtOAc | .25x | 1.0 |
| Rep 1 | BuOH | .25x | 4.0 |
| Rep 1 | Aqueous | .25x | 4.0 |
| Rep 1 | Combined | .25x | 1.0 |
| Rep 2 | Whole Broth | .25x | 2.0 |
| Rep 2 | EtOAc | .25x | 3.0 |
| Rep 2 | BuOH | .25x | 4.0 |
| Rep 2 | Aqueous | .25x | 4.0 |
| Rep 2 | Combinec | .25x | 2.0 |
| Rep 3 | Supernatant | .25x | 1.0 |
| Rep 3 | pH 1 | .25x | 4.0 |
| Rep 3 | pH 10 | .25x | 2.0 |
| Rep 3 | RP 25% MeOH | 1x | 4.0 |
| Rep 3 | RP 50% MeOH | 1x | 4.0 |
| Rep 3 | RP 75% MeOH | 1x | 4.0 |
| Rep 3 | RP 100% MeOH | 1x | 1.0 |
| Rep 3 | RP Combined | 1x | 1.0 |
| Rep 4 | WB | ½x | 1.0 |
| Rep 4 | pH 1 | ½x | 4.0 |
| Rep 4 | pH 10 | ½x | 1.0 |
| Rep 4 | Whole broth | ½x | 2.0 |
| Rep 4 | pH 1 | ½x | 4.0 |
| Rep 4 | pH 10 | ½x | 2.0 |
| Rep 4 | EtOAc | ½x | 2.0 |
| Rep 4 | RP 25% MeOH | 1x | 4.0 |
| Rep 4 | RP 50% MeOH | 1x | 4.0 |
| Rep 4 | RP 75% MeOH | 1x | 4.0 |
| Rep 4 | RP 100% MeOH | 1x | 2.0 |
| Rep 4 | RP Combined | 1x | 2.0 |

Unlike the fungicides typically associated with *Streptomyces galbus*, the insecticidal activity of NRRL Accession No. 30232 was stable under alkali conditions (pH 9–10) and unstable in acid (pH 1–2).

Example 5
Plant Activity of NRRL Accession No. 30232 Against Insect Pests

Whole plant testing confirmed the activity of NRRL Accession No. 30232 against beet armyworm. First, true leaves from young Henderson bush lima beans were dipped for 3–5 seconds in whole broth and allowed to air dry. Leaves were placed in 50 mm petri dish with damp filter paper and 10 first instar neonate beet armyworm larvae. Mortality was rated after 48 hours. The results are shown in Table 4, below.

TABLE 4

Larvicidal activity of NRRL Accession No. 30232 in leaf dip tests against beet armyworm

| Sample | Conc. | No. Alive/No. Dead | % Mortality | Average Mortality |
|---|---|---|---|---|
| NRRL 30232 | 1X WB | 3/7, 2/8, 4/6 | 70, 80, 60 | 70% |
| Javelin ® | 200 PPM | 1/9, 2/8, 1/9 | 90, 80, 90 | 87% |
| UTC (H$_2$O) | 0 | 9/1, 9/0, 7/0 | 10, 0, 0 | 3% |

In similar tests, NRRL Accession No. 30232 demonstrated equal or better larvicidal activity against *Heliothis virescens, Helicoverpa zea*, and *Anticarsia gemmatalis*.

NRRL Accession No. 30232 whole broths were spun at 9,000 xg and the supernatant was sprayed onto one-week-old Henderson Bush lima bean plants using an airbrush. The new leaves were allowed to dry and the smallest true leaves were harvested. Each leaf (three replicates per treatment) was placed in a 50 ml petri dish with a dampened filter paper and approximately 10 neonate larvae. The plates were read after 40 hours in an incubator (28±2° C., 16:8 photoperiod). Large two-week-old bean plants with fully expanded true leaves were sprayed to assess potential phytotoxicity. The results are shown in Table 5, below.

TABLE 5

Efficacy of supernatant and EtOAc extracts against beet armyworms on bean leaves

| Sample | No. Alive/No. Dead | Average Mortality |
|---|---|---|
| 30232 1x Supernatant | 1/9, 1/8, 2/7 | 89% |
| 30232 1x Ethyl Acetate | 5/1, 5/4, 4/6 | 40% |
| UTC H$_2$O | 6/1, 8/2, 8/2 | 18% |

*This is the same EtOAc extract used in the assay documented in Table 3.

No phytotoxicity was seen with any of the samples. The leaf tests support the primary screen data showing the whole broth and the supernatant to be stable and potent. In this assay the ethyl acetate fraction lost some activity when sprayed onto leaves.

Additional whole plant testing at a greenhouse scale confirmed plant protection of Chinese cabbage, *Brassica rapa*, against beet armyworm. A laboratory track sprayer (Devries Manufacturing, Holland, Mich.) was calibrated to deliver a 90-gallon/acre spray volume via a TEE-JET 8015 fan nozzle. Mature cabbage plants were treated with deionized water (negative control), NRRL Accession No. 30232 whole broth, or Javelin® WG at 1.1 lb/acre (toxic standard). Prior to application, the NRRL Accession No. 30232 whole broth was mechanically homogenized for 20 seconds with an Ultra Turrax (Tekmar, Cincinnati, Ohio). Each treatment was replicated three times. The spray residues were checked for uniformity and allowed to dry before the plants were placed within a plexiglass and mesh enclosure within a greenhouse environment. Each plant was then inoculated with approximately 50 neonate larvae and approximately 50 eggs. The plants were watered as necessary and without washing spray residue or insects from the foliage.

Qualitative observations on Day 7 indicated significant insect feeding damage within the control treatment, minor damage within the toxic standard treatment (Javelin®), and little or no damage within the NRRL Accession No. 30232 treatment. The results indicated that the NRRL Accession No. 30232 treatment resulted in plants of superior market quality.

Example 6
Fermentation Scale Up and Stability of the Activity Against Caterpillar Pests.

Fermentation scale-up issues are a significant component in the critical path of evaluating a potential biopesticide (Hofstein and Freidlender (1994) "Development of production, formulation, and delivery systems for biofungicides" In: *Brighton Crop Protection Conference: Pests and Disease*, BCPC publications, Major Print Ltd., Nottingham UK, pp. 1273–1280). Increasing the volume of the fermentation from 12 ml in a 50 ml tube (T1) to 50 ml in a 250 ml-shake flask (S1) is the first step in the scale up process. Concentration of the supernatants from this step via speed-vac did not have a negative impact on the biological activity of NRRL Accession No. 30232 yielding a positive dose response when tested at 2x, 1x, and 0.5x. Stability testing of NRRL Accession No. 30232 from S1 fermentation showed the activity against beet armyworm to be stable for two to three weeks when held under refrigeration at 4° C. or held frozen at −80° C. The results are shown in Tables 6 and 7, below.

TABLE 6

Bioactivity of one-week-old (W1) broth grown in a 250-ml shake flask (S1) and 50 ml tubes (T1)

| Media | Concentration | Vessel/Age | BAW |
|---|---|---|---|
| 31 | 0.5x Super | S1W1 | 2.0 |
| 31 | 1x Super | S1W1 | 2.0 |
| 31 | 2x Super | S1W1 | 1.0 |
| 31 | 1x Super | T1W1 | 2.0 |
| 31 | 1x Super | S1W1 | 1.0 |
| 38 | 0.5x Super | S1W1 | 4.0 |
| 38 | 1x Super | S1W1 | 2.0 |
| 38 | 2x Super | S1W1 | 2.0 |
| 38 | 1x Super | T1W1 | 2.0 |
| 38 | 1x Super | S1W1 | 2.0 |

TABLE 7

Bioactivity of two-week old (W2) 30232 broth grown in a 250-ml shake flask (S1)

| Media | Concentration | Vessel/Age | CE | CRW | BAW | GPA | SM |
|---|---|---|---|---|---|---|---|
| 31 | 0.5x Super | S1W2 | | | 1.0 | | |
| 31 | 1x Super | S1W2 | | | 1.0 | | |
| 31 | 2x Super | S1W2 | | | 1.0 | | |
| 31 | 2x Super | S1W2 | 4.0 | 4.0 | 1.0 | 3.0 | 0 |
| 38 | 0.5x Super | S1W2 | | | 4.0 | | |
| 38 | 1x Super | S1W2 | | | 1.0 | | |
| 38 | 2x Super | S1W2 | | | 1.0 | | |
| 38 | 2x Super | S1W2 | 4.0 | 4.0 | 1.0 | 4.0 | 0 |

Table 8, below, shows the results when the specificity of the biological activity from the 250 ml flask was limited to beet armyworm as in the initial 50 ml tube fermentation.

TABLE 8

Bioactivity of three-week old (W3) refrigerated and frozen NRRL Accession No. 30232 broth grown in a 250 ml shake flask (S1)

| Media | Concentration | Vessel/Age/Temp | BAW |
|---|---|---|---|
| 31 | 1x | S1W3-80° C. | 2.0 |
| 31 | 1x | S1W3-4° C. | 2.0 |
| 38 | 1x | S1W3-80° C. | 3.0 |
| 38 | 1x | S1W3-4° C. | 3.0 |

The second step in the scale up process is a repeat of the 50 ml volume in a 250 ml flask (S2). Concurrent fermentation in a 50-ml tube verified activity of the strain. Results are shown in Table 9, below.

TABLE 9

Response of one-week-old (W1) broth grown in a 250-ml shake flask (S2) and 50 ml tubes (T2)

| Media | Concentration | Vessel | BAW |
|---|---|---|---|
| 31 | 1x Supernatant | S2W1 | 1.0 |
| 31 | 1x Supernatant | T2W1 | 2.0 |
| 31 | 1x Supernatant | S2W1 | 1.0 |
| 38 | 1x Supernatant | S2W1 | 3.0 |
| 38 | 1x Supernatant | T2W1 | 1.0 |
| 38 | 1x Supernatant | S2W1 | 4.0 |

As the volume increased, the bioactivity of media 38 declined compared to media 31. Sigmund J. M. and Hirsch, C. F. (1998) *J. Antibiotics* 51:829–836, demonstrated the addition of tomato paste to be a critical component in the production of fungicidal activity. In contrast to what is seen with rustmicin (produced by *S. galbus*), our scale-up showed that as the volume increased, the complex oat flour media (31) increased the insecticidal activity of NRRL Accession No. 30232 over the tomato paste-based media 38. Two additional increases in volume confirmed the efficacy of media 31. The S3 utilized 200 ml of media 31 in baffled 1 L flask and the S4 utilized 500 ml volumes in un-baffled 2.8 L Fernbach flasks. The results are shown in Table 10, below.

TABLE 10

Bioactivities of two-week-old (W2) broths grown in 1,000-ml shake flasks (S3) and 2,800 ml Fernbach flasks (S4)

| Replicate | Media | Concentration | Vessel/Age | BAW |
|---|---|---|---|---|
| Rep 1 | 31 | 0.5x Supernatant | S3W2 | 3.0 |
| Rep 1 | 31 | 1x Supernatant | S3W2 | 2.0 |
| Rep 1 | 31 | 2x Supernatant | S3W2 | 2.0 |
| Rep 1 | 31 | 0.5x Supernatant | S4W2 | 2.0 |
| Rep 1 | 31 | 1x Supernatant | S4W2 | 1.0 |
| Rep 2 | 31 | 0.5x Supernatant | S4W2 | 4.0 |
| Rep 2 | 31 | 1x Supernatant | S4W2 | 2.0 |
| Rep 2 | 31 | 2x Supernatant | S4W2 | 2.0 |

Increasing the size of the fermentation through three steps to 500 ml of media 31 in a 2800 ml Fernbach flask did not have a negative impact on the insecticidal activity of NRRL Accession No. 30232.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

We claim:

1. An isolated *Streptomyces galbus* strain selected from the group consisting of a *Streptomyces galbus* strain having all the identifying characteristics of the *Streptomyces galbus*, strain deposited with NRRL as Accession No. 30232, variants of the strain deposited with NRRL as Accession No. 30232, wherein the variants have all the identifying characteristics of the NRRL No. 30232 strain; and mutants of the strain deposited with NRRL as Accession No. 30232, wherein the mutants have all the identifying characteristics of the NRRL No. 30232 strain; and wherein one of the identifying characteristics of the NRRL No. 30232 strain is that a supernatant isolated from a whole broth culture of the NRRL No. 30232 strain has insecticidal activity against beet armyworm and has minimal or no acaricidal activity against two-spotted spider mites.

2. A composition comprising the strain of claim 1, and at least one chemical or biological pesticide.

3. An isolated *Streptomyces galbus* strain having all the identifying characteristics of the *Streptomyces galbus* strain deposited with NRRL as Accession No. 30232; wherein one of the identifying characteristics of the NRRL No. 30232 strain is that a supernatant isolated from a whole broth culture of the NRRL No. 30232 strain has insecticidal activity against beet armyworm and has minimal or no acaricidal activity against two-spotted spider mites.

4. A composition comprising the strain of claim 3, and at least one chemical or biological pesticide.

5. A composition comprising the isolated *Streptomyces galbus* strain of claim 1 or 2 and a carrier.

6. The composition of claim 5, wherein the composition is formulated from the group consisting of a wettable powder, a granule, an aqueous suspension, an emulsifiable concentrate, and a microencapsulated formulation.

7. A culture comprising the strain of claim 1 or claim 3.

8. A method for preventing or treating a plant, root or fruit from an insect infestation comprising applying an effective amount of the culture of claim 7 to the plant, root or fruit.

9. The method of claim 8, wherein the insect is selected from the group consisting of Lepidoptera, Coleoptera and Diptera.

10. The method of claim 9, wherein the insect is Lepidoptera.

11. The method of claim 10, wherein the Lepidoptera infestation is caused by at least one insect selected from the group consisting of *Spodoptera exigu, Anticarsia gemmatalis*, Pluteila spp., *Helicoverpa zea, Heliothis virescens*, and *Trichoplusia ni.*

12. A method for preventing or treating a plant, root or fruit from an insect infestation comprising applying an effective amount of the isolated strain of claim 1 or 3 to the plant, root or fruit.

13. The method of claim 12, wherein the insect is selected from the group consisting of Lepidoptera, Coleoptera and Diptera.

14. The method of claim 12, wherein the insect is Lepidoptera.

15. The method of claim 14, wherein the Lepidoptera infestation is caused by at least one insect selected from the group consisting of *Spodoptera exigua, Anticarsia gemmatalis*, Plutella spp., *Helicoverpa zea, Heliothis virescens*, and *Trichoplusia ni.*

16. A method for preventing or treating a plant, root or fruit from an insect infestation comprising applying an effective amount of the composition of claim 2 or 4 to the plant, root or fruit.

17. The method of claim 16, wherein the insect is selected from the group consisting of Lepidoptera, Coleoptera and Diptera.

18. The method of claim 17, wherein the insect is Lepidoptera.

19. The method of claim 18, wherein the Lepidoptera infestation is caused by at least one insect selected from the group consisting of *Spodoptera exigua, Anticarsia gemmatalis*, Plutella spp., *Helicoverpa zea, Heliothis virescens*, and *Trichoplusia ni.*

* * * * *